(12) United States Patent
Zou et al.

(10) Patent No.: US 11,497,719 B1
(45) Date of Patent: Nov. 15, 2022

(54) CANNABINOID COMPOSITION AND APPLICATION OF THE SAME IN PREPARING MEDICINE FOR TREATING NEURODEGENERATIVE DISEASES INCLUDING PARKINSON'S DISEASE AND ALZHEIMER'S DISEASE

(71) Applicants: Chendong Zou, Shanghai (CN); Hei Tai, Shanghai (CN); Guijiang Wang, Shanghai (CN); Wan Xiao, Shanghai (CN); Sui Huang, Shanghai (CN)

(72) Inventors: Chendong Zou, Shanghai (CN); Hei Tai, Shanghai (CN); Guijiang Wang, Shanghai (CN); Wan Xiao, Shanghai (CN); Sui Huang, Shanghai (CN)

( * ) Notice: Subject to any disclaimer, the term of this patent is extended or adjusted under 35 U.S.C. 154(b) by 0 days.

(21) Appl. No.: 17/586,304

(22) Filed: Jan. 27, 2022

(30) Foreign Application Priority Data

Aug. 11, 2021 (CN) .......................... 202110916566.9

(51) Int. Cl.
| | | |
|---|---|---|
| *A61K 31/05* | (2006.01) | |
| *A61P 25/16* | (2006.01) | |
| *A61P 25/28* | (2006.01) | |

(52) U.S. Cl.
CPC .............. *A61K 31/05* (2013.01); *A61P 25/16* (2018.01); *A61P 25/28* (2018.01)

(58) Field of Classification Search
CPC ................................ A61K 31/05; A61P 25/28
See application file for complete search history.

(56) References Cited

U.S. PATENT DOCUMENTS

2010/0239693 A1* 9/2010 Guy ........................ A61P 25/28
514/456

FOREIGN PATENT DOCUMENTS

| CN | 107095302 A | 8/2017 |
|---|---|---|
| WO | 2018-071452 A1 | 4/2018 |

OTHER PUBLICATIONS

Mammana et al. Medicinia 2019, 55, 747 (Year: 2019).*
Di Giacomo et al. Int. J. Mol. Sci. 2020, 21, 3575 (Year: 2020).*
Velayudhan et al., Current Pharmaceutical Design, 2014, 20, 2218-2230. (Year: 2014).*
Robaina Cabrera et al., "The Anti-Inflammatory Effects of Cannabidiol and Cannabigerol Alone, and in Combination," Pulmonary Pharmacology & Therapeutics, vol. 69, 102047, Jun. 1, 2021, 10 pages.
Echeverry et al., "A Comparative In Vitro Study of the Neuroprotective Effect Induced by Cannabidiol, Cannabigerol, and Their Respective Acid Forms: Relevance of the 5-HT 1A Receptors," published online Sep. 4, 2020, Neurotoxicity Research, 2021, vol. 39, pp. 335-348.
Marsicano et al., "Neuroprotective Properties of Cannabinoids Against Oxidative Stress: Role of the Cannabinoid Receptor CB1," Journal of Neurochemistry, 2002, vol. 80, pp. 448-456.

* cited by examiner

*Primary Examiner* — Kamal A Saeed
(74) *Attorney, Agent, or Firm* — Amster, Rothstein & Ebenstein LLP (57) ABSTRACT

Disclosed are a cannabinoid composition and an application of the same in preparing a medicine for treating neurodegenerative diseases, so as to solve the drawbacks of conventional medicines such as serious side effects and degraded therapeutic effect after long-term administration. The cannabinoid composition includes: cannabidiol and cannabigerol, a mass ratio of the cannabidiol to the cannabigerol ranging from 1:1 to 1:10, or from 1:0.3 to 1:0.5, or from 1:0.5 to 1:0.7, or from 1:07 to 1:1. The present disclosure adopts the experimental method of inducing differentiation of fibroblasts to dopaminergic neurons, wherein by observing the cell morphology, quantity, and relative expression level of DA-related factor of the differentiation-induced and cultured fibroblasts, and screening various common cannabinoids and different combinations thereof based on their impacts on inducing differentiation of the fibroblasts into dopaminergic neurons, it was found that the CBD+CBG combination offered an optimal effect in improving viability and dopamine-secreting capability of the dopaminergic neuronal cells; besides, the CBD+CBG combination is free of the addictive substance THC, which thus significantly reduces side effects and may be applied to prepare medicines for treating neurodegenerative diseases.

14 Claims, 6 Drawing Sheets

Specification includes a Sequence Listing.

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: Primer No. 1

<400> SEQUENCE: 1
actgccgatt tcagaagtgc                                              20

<210> SEQ ID NO 2
<211> LENGTH: 22
<212> TYPE: DNA
<213> ORGANISM: Artificial Sequence
<220> FEATURE:
<223> OTHER INFORMATION: Primer No. 2
```

```
<400> SEQUENCE: 2
ccggcctttt aaactgtctg tg                                              22

<210> SEQ ID NO 3
<211> LENGTH: 22
<212> TYPE: DNA
<213> ORGANISM: Artificial Sequence
<220> FEATURE:
<223> OTHER INFORMATION: Primer No. 3

<400> SEQUENCE: 3
gagtacaccg ccgaggagat tg                                              22

<210> SEQ ID NO 4
<211> LENGTH: 22
<212> TYPE: DNA
<213> ORGANISM: Artificial Sequence
<220> FEATURE:
<223> OTHER INFORMATION: Primer No. 4

<400> SEQUENCE: 4
gcggatatac tgggtgcact gg                                              22

<210> SEQ ID NO 5
<211> LENGTH: 20
<212> TYPE: DNA
<213> ORGANISM: Artificial Sequence
<220> FEATURE:
<223> OTHER INFORMATION: Primer No. 5

<400> SEQUENCE: 5
agcacagcga ctcagaaaag                                                 20

<210> SEQ ID NO 6
<211> LENGTH: 20
<212> TYPE: DNA
<213> ORGANISM: Artificial Sequence
<220> FEATURE:
<223> OTHER INFORMATION: Primer No. 6

<400> SEQUENCE: 6
tttttcagcg aaccgtcctc                                                 20
```

CANNABINOID COMPOSITION AND APPLICATION OF THE SAME IN PREPARING MEDICINE FOR TREATING NEURODEGENERATIVE DISEASES INCLUDING PARKINSON'S DISEASE AND ALZHEIMER'S DISEASE

CROSS-REFERENCE TO RELATED APPLICATIONS

This application claims priority to and the benefit of Chinese Patent Application No. 202110916566.9, filed Aug. 11, 2021, the contents of which are hereby incorporated by reference.

FIELD

This invention concerns the field of medicines, and more specifically concerns a cannabinoid composition and an application of the same in preparing a medicine for treating neurodegenerative diseases including Parkinson's disease and Alzheimer's disease.

BACKGROUND

Neurodegenerative diseases including Parkinson's disease (PD), Alzheimer's disease (AD), and dementia with Lewy bodies (DLB) are an increasing health burden for older populations. Among the people aged 80 or older, one out of every two suffer from AD, whose mortality rate is only second to heat attacks, tumors, and strokes. The prevalence rate of PD is 1%~2% among people aged 65 or older, and around 4% among people aged 85 or older.

Through long-term research, it is gradually revealed that such neurodegenerative diseases are related to dopamine metabolism disorders and shedding-induced decrease of dopamine-secreting nerve cells. Neuritic plaques outside neurons and fibrillary tangles inside neurons are typical pathological changes of AD. Currently, AD is mainly treated with choline esterase inhibitor. However, it has been found that dopamine as a neurotransmitter also participates in the course of AD. Decrease levels of dopamine, L-DOPA and metabolites in parts such as striatum, amygdala and substantia nigra can be seen from autopsy of AD patients.

The characteristic pathological changes of PD include degeneration and death of massive dopaminergic (DA) neurons in the mesencephalic substantia nigra, and formation of Lewy bodies in the residual neuron cytoplasm. Currently, conventional PD therapies mainly include medical therapies and surgical therapies. Medical therapies include dopamine replacement therapy, anticholinergic agents, dopamine receptor agonists, monoamine oxidase inhibitors, catechol-o-methyltransferase inhibitors, glutamate receptor antagonists, etc., wherein levodopa is a common medicine for PD. Levodopa is believed to be the most effective medicine for treating PD. However, after long-term use, many medicines, including levodopa, not only cause decreased efficacy, but also lead to various complications such as on-off phenomenon, wearing off phenomenon and dyskinesia.

Therefore, a medicine with remarkable and long-lasting efficacy, and little side effect is desirable.

SUMMARY

Embodiments of the present disclosure provide a cannabinoid composition and an application of the same in preparing a medicine for treating neurodegenerative diseases so as to solve the above and other problems of conventional medicines for treating neurodegenerative diseases such as serious side effects and decreased efficacy after long-term use.

Cannabidiol, or CBD, is a non-toxic phenolic compound extracted from cannabis flowers and leaves, that has a high added value and can be applied in medicinal products, cosmetics, and health food. Now, CBD has been used as an active pharmaceutical ingredient and a plurality of CBD-related specialty medicines have been developed in the USA and UK. CBD, as a non-addictive ingredient found in cannabis, can inhibit THC's influence on human nervous system and has pharmacological activities such as anti-spasticity, anti-rheumatic arthritis and anti-anxiety. Its application to treat PD has also been reported; however, the therapeutic effect of using the CBD alone is not satisfactory. Although compound cannabinoid compositions have also been studied, most of the compositions include an addictive substance THC. Considering that controls on THC are imposed more or less in various countries, it is more important to develop a novel THC-free therapeutic medicine which has a good therapeutic effect and minor side effects.

Cannabinol, or CBN, is a cannabinoid derived from oxidation and decomposition of THC, with significantly reduced psycho-activity.

Cannabigerol, or CBG, is a precursor of other cannabinoids (such as CBD and THC), characterized by high therapeutic effect, no psycho-toxicity or other side effects. Currently, although extensive research has been conducted on the applications of CBD and THC in treating neurodegenerative diseases, there are few reports and studies on the therapeutic effects of CBG.

In view of the above, a first objective of the present disclosure is to provide a cannabinoid composition, comprising: cannabidiol and cannabigerol, wherein a mass ratio of the cannabidiol to the cannabigerol ranges from 1:1 to 1:10, or from 1:0.3 to 1:0.5, or from 1:0.5 to 1:0.7, or from 1:07 to 1:1.

Preferably, the mass ratio of the cannabidiol to the cannabigerol ranges from 1:1 to 1:3, or from 1:3 to 1:5, or from 1:5 to 1:7.

Preferably, the cannabinoid composition further comprises cannabinol.

Preferably, the mass ratio of the cannabidiol to the cannabinol ranges from 1:0.05 to 1:1.

Preferably, the mass ratio of the cannabidiol to the cannabinol ranges from 1:0.1 to 1:0.5.

Preferably, a mass ratio between the cannabidiol, the cannabigerol, and cannabinol is 1:3:0.3.

Another objective of the present disclosure is to provide an application of the cannabinoid composition in preparing a medicine for treating neurodegenerative diseases.

preferably, the neurodegenerative diseases include Parkinson's disease, Alzheimer's disease and dementia with Lewy bodies;

the cannabinoid composition is applied to promote development and maturity of dopaminergic neuronal cells, preventing shedding of the dopaminergic neuronal cells and enhancing viability of the dopaminergic neuronal cells;

the cannabinoid composition is applied to enhance dopamine-secreting capability of dopaminergic neuronal cells.

A further objective of the present disclosure is to provide a pharmaceutical composition for treating neurodegenerative diseases, the pharmaceutical composition comprising: the cannabinoid composition, and a pharmaceutically acceptable carrier.

A dosage form of the pharmaceutical composition includes: oil agent, granule, tablet, pulvis, capsule, pill, powder, oral liquid, gel, spray, and aerosol.

A still further objective of the present disclosure is to provide a pharmaceutical kit for treating neurodegenerative diseases, the pharmaceutical kit comprising: the cannabinoid composition.

Compared with the prior art, the present disclosure offers the following beneficial effects:

(1) The present disclosure adopts the experimental method of inducing differentiation of fibroblasts to dopaminergic neurons, wherein by observing the cell morphology, amount, and relative expression level of DA-related factor of the differentiation-induced and cultured fibroblasts, and screening various common cannabinoids and different combinations thereof based on their impacts on inducing differentiation of the fibroblasts into dopaminergic neurons, it was found that the CBD+CBG combination offered an optimal effect in improving viability and dopamine-secreting capability of the dopaminergic neuronal cells, which may be applied to prepare medicines for treating neurodegenerative diseases, e.g., Parkinson's disease. By further designing experiments on combinations of different proportions of CBD and CBG, it was found that when the CBD+CBG combination offers a better effect and safety when the mass ratio of CBD to CBG ranges from 1:1 to 1:5, wherein the optimal mass ratio is 1:3.

(2) The CBD+CBG combination offers the optimal effect and is free of the addictive substance THC, which thus significantly reduces side effects after being used as medicine ingredients; since medicine abuse is not a worry, a major barrier in application is eliminated.

(3) The CBD+CBG composition provided by the present disclosure can significantly improve the relative expression levels of Pitx3 and TH-2, i.e., improving viability of the dopaminergic neuronal cells and the ability of secreting dopamine. This mechanism of action is better than conventional PD treatment options (e.g., oral levodopa). Long-term administration of the CBD+CBG composition does not produce the side effects similar to levodopa, and the therapeutic effect is not degraded. Meanwhile, due to different mechanisms of action, the CBD+CBG composition may be theoretically co-administered with medicines such as levodopa, achieving a better therapeutic effect or significantly deferring the side effects of long-term administration of levodopa.

(4) The present disclosure further designs experiments on combinations of different proportions of CBD+CBG+CBN, finding that adding of the CBN further enhances the cannabinoid composition's effect in activating vitality of the dopaminergic neuronal cells, wherein the effect of activating vitality of the dopaminergic neuronal cells is the optimal when CBD:CBG:CBN (mass ratio) is 1:3:0.3.

BRIEF DESCRIPTION OF THE DRAWINGS

FIG. 2 shows relative expression levels of DA-related factors of respective groups of cells in the first example of the present disclosure, wherein:
A denotes the detection result of Nurr1 expression;
B denotes the detection result of TH-2 expression;
C denotes the detection result of Pitx3 expression.

In FIGS. 1~2, Cont denotes the non-differentiated group; 6CD denotes the differentiated control group; 6CD+d denotes the differentiated+CBD group; 6CD+g denotes the differentiated+CBG group; 6CD+t denotes differentiated+THC group; 6CD+dg denotes the differentiated+CBD+CBG group; 6CD+dt denotes the differentiated+CBD+THC group.

FIG. 3 is a micrograph in lieu of a drawing, showing cell morphology of the differentiated and cultured HDF38 fibroblasts in the second example of the present disclosure, wherein:
A is the cell morphology image on the $4^{th}$ day of induction and culturing;
B is the cell morphology image on the $7^{th}$ day of induction and culturing;
C is the cell morphology image on the $13^{th}$ day of induction and culturing.

FIG. 4 illustrates relative expression levels of DA-related factors of respective groups of cells in the second example of the present disclosure, wherein:
A denotes the detection result of Nurr1 expression;
B denotes the detection result of TH-2 expression;
C denotes the detection result of Pitx3 expression.

In FIGS. 3-4, Cont denotes the non-differentiated group; 6CD denotes the differentiated control group; 6CD+dg0.1 denotes adding CBD and CBG with a mass ratio of 1:0.1; 6CD+dg0.3 denotes adding CBD+CBG with a mass ratio of 1:0.3; CBD+dg0.5 denotes adding the CBD and CBG with a mass ratio of 1:0.5; 6CD+dg0.7 denotes adding the CBD and CBG with a mass ratio of 1:0.7; 6CD+dg1 denotes adding the CBD and CBG with a mass ratio of 1:1; 6CD+dg3 denotes adding the CBD and CBG with a mass ratio of 1:3; 6CD+dg5 denotes adding the CBD and CBG with a mass ratio of 1:5; 6CD+dg7 denotes adding the CBD and CBG with a mass ratio of 1:7; 6CD+dg10 denotes adding the CBD+CBG with a mass ratio of 1:10; and 6CD+dt denotes differentiated+CBD+THC group.

FIG. 5 illustrates relative expression levels of DA-related factors of respective groups of cells in the third example of the present disclosure, wherein:
A denotes the detection result of Nurr1 expression;
B denotes the detection result of TH-2 expression;
C denotes the detection result of Pitx3 expression.

In FIG. 5, Cont denotes non-differentiated group; 6CD denotes the differentiated control group; 6CD+dg1 denotes adding CBD and CBG with a mass ratio of 1:1; 6CD+dg1+n0.1 denotes adding CBD, CBG and CBN with a mass ratio of 1:1:0.1; 6CD+dg1+n0.3 denotes adding the CBD, CBG and CBN with a mass ratio of 1:1:0.3; 6CD+dg1+n0.5 denotes adding the CBD, CBG and CBN with a mass ratio of 1:1:0.5; 6CD+dg3 denotes adding the CBD and CBG with a mass ratio of 1:3; 6CD+dg3+n0.1 denotes adding the CBD, CBG and CBN with a mass ratio of 1:3:0.1; 6CD+dg3+n0.3 denotes adding the CBD, CBG and CBN with a mass ratio of 1:3:0.3; 6CD+dg3+n0.5 denotes adding the CBD, CBG and CBN with a mass ratio of 1:3:0.5.

DETAILED DESCRIPTION

Hereinafter, the technical solution of the present disclosure will be further illustrated through embodiments with reference to the accompanying drawings.

Embodiments of the present disclosure provide a cannabinoid composition, comprising: cannabidiol and cannabigerol, a mass ratio of the cannabidiol to the cannabigerol ranging from 1:1 to 1:10; preferably, the mass ratio of the cannabidiol to the cannabigerol ranges from 1:1 to 1:3, or from 1:3 to 1:5, or from 1:5 to 1:7; more preferably, the mass ratio of the cannabidiol to the cannabigerol is 1:3.

The cannabinoid composition further comprises cannabinol, a mass ratio of the cannabidiol to the cannabinol ranging from 1:0.05 to 1:1; preferably, the mass ratio of the cannabidiol to the cannabinol ranges from 1:0.1 to 1:0.5; more preferably, the mass ratio between the cannabidiol, the cannabigerol, and cannabinol is 1:3:0.3.

Experiments revealed that the cannabinoid composition provided by the present disclosure could, on one hand, promote development and maturity of dopaminergic neuronal cells, prevent shedding of the dopaminergic neuronal cells, and enhance viability of the dopaminergic neuronal cells; and on the other hand, may enhance dopamine-secreting capability of the dopaminergic neuronal cells. Therefore, the cannabinoid composition may be applied to prepare medicines for the treatment of neurodegenerative diseases, wherein the neurodegenerative diseases include Parkinson's disease, Alzheimer's disease, and dementia with Lewy bodies.

Embodiments of the present disclosure further provide a pharmaceutical composition for treating neurodegenerative diseases, the pharmaceutical composition comprising: the cannabinoid composition according to the present disclosure, and a pharmaceutically acceptable carrier.

Appropriate pharmaceutically acceptable carriers are known to those skilled in the art. Detailed introductions on pharmaceutically acceptable carriers may be found in Remington's Pharmaceutical Sciences. The pharmaceutically acceptable carriers for compositions may include liquid such as water, phosphate buffer, ringer solution, physiological saline, balanced salt solution, glycerin or sorbitol, etc. Additionally, the carriers may further include auxiliary substances, such as lubricants, glidants, wetting agents or emulsifiers, pH buffering substances and stabilizers, e.g., albumin. In use, a safe and effective amount of the cannabinoid composition is applied to mammals (such as humans). Of course, specific dosage shall also take factors such as the route of administration and patient health condition into consideration, which are technically known to those skilled physicians. An accurate effective dosage for a subject depends on body shape and health status of the subject, nature and degree of the disease, and the therapeutic agent and/or combination of therapeutic agents selected for administration. For a given condition, the effective dosage can be determined through routine experiments and can be figured out by clinicians.

A dosage form of the pharmaceutical composition includes: oil agent, granule, tablet, pulvis, capsule, pill, powder, oral liquid, gel, spray, and aerosol.

Embodiments of the present disclosure further provide a pharmaceutical kit for treating neurodegenerative diseases, the pharmaceutical kit comprising: the cannabinoid composition or the pharmaceutical composition according to the present disclosure.

To facilitate clinical application, the pharmaceutical composition of the present disclose may be included in an injection applicator (such as an injection needle), and the injection applicator may include a single dose of the pharmaceutical composition. The injection applicator may be included in a pharmaceutical kit to facilitate storage and use. The pharmaceutical kit of the present disclosure may also include a use instruction so as to facilitate proper use of those skilled in the art.

Hereinafter, the experimental processes and experimental results of the present disclosure will be illustrated in detail through the embodiments with reference to the accompanying drawings, describing in detail activation of the cannabinoid composition of the present disclosure with respect to the dopaminergic neuronal cells, and medicines applicable to prepare neurodegenerative diseases including Parkinson's disease, Alzheimer's disease and dementia with Lewy bodies.

Related Testing Proteins in the Examples:

Nurr1: nuclear receptor related protein1, which is a member of the nuclear receptor superfamily of intracellular transcription factors and is critical in maintenance of the cerebral dopaminergic system. Mutation of this gene is related to dopaminergic dysfunctions, including Parkinson's disease, schizophrenia and manic-depressive psychosis. The Nurr1 protein is believed to be essential in the development of midbrain dopaminergic phenotype.

Pitx3: a protein transcribed from the PITX3 gene. Pitx3 is specifically expressed in cerebral dopaminergic neurons, which plays a critical role in the differentiation and maturation of cerebral dopaminergic neurons, and is believed as a transcription factor essential for specific development of midbrain dopaminergic neurons.

TH: Tyrosine hydroxylase, which is the key enzyme in the biosynthesis of dopamine. PD is a neurodegenerative disease caused by severe dopamine deficiency in the substantia nigra and striatum. The expression regulation of TH plays an important role in PD development and treatment.

In the process of differentiation into dopaminergic neuronal cells, first, after the expression of Nurr1 is maintained at a certain level, TH and Pitx3 are expressed. As only the expression of Nurr1 can induce the expression of the marker genes TH and Pitx3 to promote further differentiation and maturation of cells. Therefore, to a certain extent, expression of TH and Pitx3 is more important, because their expression capability can better reflect vitality of dopaminergic neuronal cells.

Example 1

Experiment Process
1. Preparing Culture Mediums
Basal Medium 1: DMEM medium, including 10% FBS and 1% Penicillin Streptomycin.
Basal Medium 2: Neurobasal medium, including 1% N-2 supplement and 1% Penicillin Streptomycin Glutamine.
Induction Medium 1: Neurobasal medium, including 1% N-2 supplement, 1% Penicillin Streptomycin Glutamine, 5% glutamine, 1% B27, 10 ng/ml bFGF, 20 ng/ml EFG, 50 ng/ml GDNF, 2 µM RA; 10 µM SB431542; 200 ng/ml Noggin.
Induction Medium 2: Neurobasal medium, including 1% N-2 supplement, 1% Penicillin Streptomycin Glutamine, 1% B27, 10 ng/ml bFGF, 20 ng/ml EFG, 50 ng/ml GDNF, 2 µM RA; 100 ng/ml SHH; 100 ng/ml FGF8b.
The culture mediums were prepared according to the above formulae; the prepared culture mediums were then sterilized via membrane filters for later use.

2. Culturing HDF38 Fibroblasts
After the purchased HDF38 fibroblasts were resuscitated and cultured, they were subcultured in seven 6 cm culture dishes including basal medium 1, wherein each culture dish included 80,000 HDF38 fibroblasts, which were cultured in a 5% $CO_2$ incubator at 37° C. After 3 days of culture, induced-differentiation of the cells were performed.

3. Inducing Differentiation of HDF38 Fibroblasts
Experiment Method: the cells were removed out of the basal medium 1 and washed with PBS for 3 times to wash off the residual medium. Then, the cells were induced to differentiate and cultured: firstly, induction mediums 1 including respective to-be-tested medicines were applied, wherein the liquids were completely replaced every 2.5 days; culturing at this stage lasted 7 days; 7 days later, the culture mediums were changed to induction mediums 2 including respective to-be-tested medicines, wherein the liquids were completely changed every 3 days; culturing at this stage lasted 6 days.

During the process of induced differentiation, the morphological changes of cells were observed with a microscope (ZEISS AXIO observer) every day, and photographed for records. The serial numbers for the 7 experiments and the ingredients of culture mediums are shown in Table 1 below.

TABLE 1

Experimental Design of different cannabinoids and their combinations

| No. | Group # | Culture Medium | To-be-tested medicine added |
|---|---|---|---|
| 1 | Non-differentiated group | Basal Medium 2 | N/A |
| 2 | Differentiated control group | Induction mediums 1, 2 | N/A |
| 3 | Differentiated + CBD group | Induction mediums 1, 2 | CBD (1 μg/10 ml culture medium) |
| 4 | Differentiated + CBG group | Induction mediums 1, 2 | CBG (1 μg/10 ml culture medium) |
| 5 | Differentiated + THC group | Induction mediums 1, 2 | THC (0.2 μg/10 ml culture medium) |
| 6 | Differentiated + CBD + CBG group | Induction mediums 1, 2 | CBD (1 μg/10 ml culture medium) and CBG (1 μg/10 ml culture medium) |
| 7 | Differentiated + CBD + THC group | Induction mediums 1, 2 | CBD (1 μg/10 ml culture medium) and THC (0.2 μg/10 ml culture medium) |

Note:
the CBG solution and CBD solution were purchased from SIGMA-ALDRICH, and Δ 9-THC was purchased from FUJIFILM.

4. Detecting the Relative Expression Level of DA-Related Factors.

After 13 days of induced differentiation and culture, the cells were collected, and the Total RNA was extracted from the cells using TRIzol general reagent (Tiangen Biotech, Beijing, China), and the Total RNA was synthesized into complementary DNA (cDNA). The relative expression levels of DA-related factors Nurr1, TH-2 and Pitx3 in the cells were detected by quantitative real-time PCR with SYBR Green fluorescent dye.

The following primer amplified segments are used:
Primer sequence of Nurr1 gene:
F: 5'-ACTGCCGATTTCAGAAGTGC-3'(SEQ ID NO:1),
R: 5'-CCGGCCTTTTAAACTGTCTGTG-3'(SEQ ID NO:2);
Primer sequence of TH gene:
F: 5'-GAGTACACCGCCGAGGAGATTG-3'(SEQ ID NO:3),
R: 5'-GCGGATATACTGGGTGCACTGG-3'(SEQ ID NO:4);
Primer sequence of Pitx3 gene:
F: 5'-AGCACAGCGACTCAGAAAAG-3'(SEQ ID NO:5),
R: 5'-TTTTTCAGCGAACCGTCCTC-3'(SEQ ID NO:6).
The conditions of qRT-PCR reaction included: 95° C., 10 minutes; 95° C., 15 seconds; 30° C., 1 minute; 40 cycles. Upon termination of the reaction, the mRNAs of the gene of interest and the reference gene were analyzed.

Figure 1:
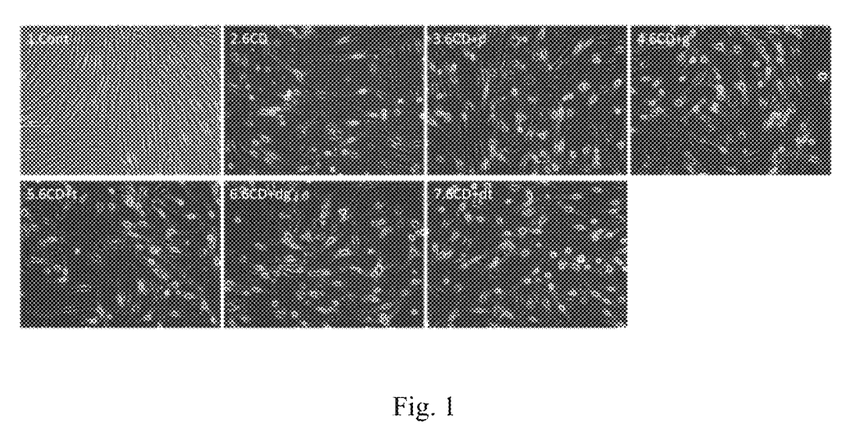
FIG. 1 is a micrograph in lieu of a drawing, showing cell morphology of the HDF38 fibroblasts differentiated and cultured on the $13^{th}$ day in the first example of the present disclosure.

(2) Experiment Results:
1. Influence of Cannabinoid Composition on Cell-Induced Differentiation The morphologies of the cells in respective culture groups were observed under microscope. The results are shown in FIG. 1: the HDF38 fibroblasts were successfully differentiated into dopaminergic neurons, and the cells induced and cultured with addition of the cannabinoid-based medicines were differentiated to a larger number of dopaminergic neurons. The above results indicate that cannabinoid-based medicines can promote differentiation of the HDF38 fibroblasts to dopaminergic neurons, wherein the CBD+CBG group has the largest number of dopaminergic neurons, indicating that CBD+CBG composition has the strongest effect in promoting differentiation of fibroblasts to dopaminergic neurons.

2. Influence of Cannabinoid Composition on Expression of DA-Related Factors

Figure 2A:
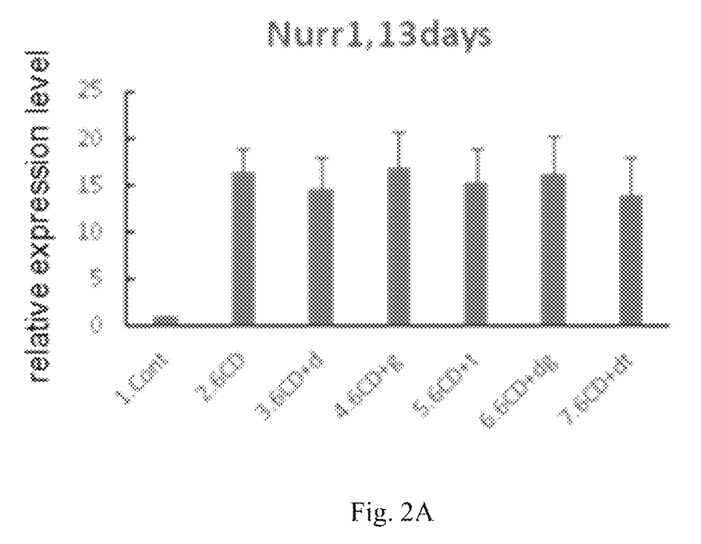

As shown in FIG. 2, all of the six groups of differentiated and cultured cells had successfully expressed the dopaminergic neuron marker genes Nurr1, TH-2 and Pitx3, among which, the Nurr1 expression levels of the six groups of induced cells were all markedly higher than the Cont group, indicating that in the experiment, the HDF38 fibroblasts had been successfully induced to differentiate to dopaminergic neurons (see A in FIG. 2).

Figure 2B:
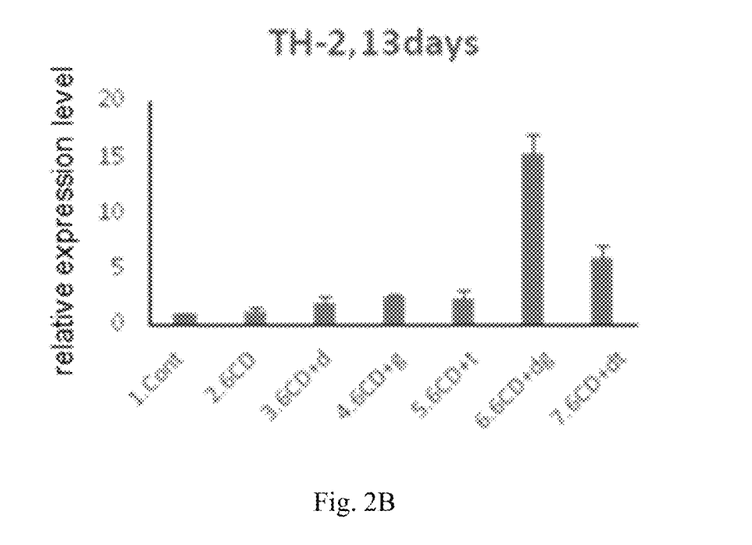
Figure 2C:
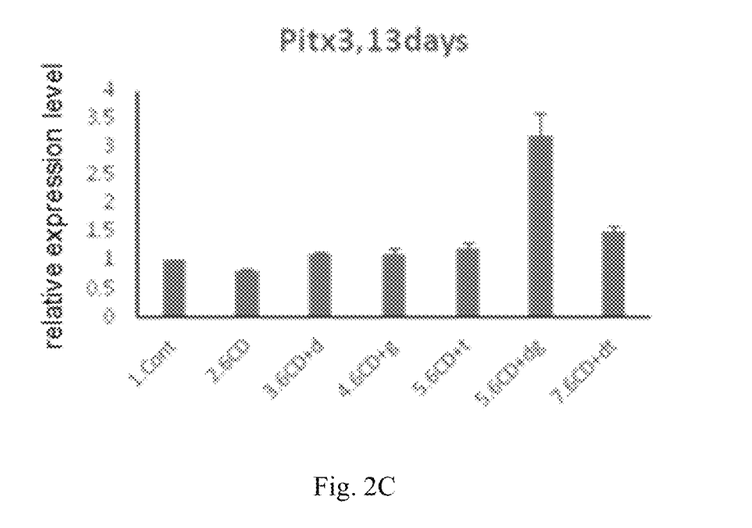

After Nurr1 was successfully expressed, the marker genes TH-2 and Pitx3 were then expressed. The expression capabilities of the two genes can better reflect the viability and vitality of dopaminergic neurons. The results showed that the expression levels of TH-2 and Pitx3 in the CBD+CBG group and the CBD+THC group were obviously superior to other groups, which indicated that compared with a single-medicine formulation, the ingredients in each of the two kinds of medicine combinations had a synergistic effect with each other and thus can play a better role in promoting development, maturity, and secretion capability of the dopaminergic neurons, wherein the TH-2 expression level of the CBD+CBG group is about 3 times higher than that of the CBD+THC group, and the Pitx3 expression level of the former is about 2 times higher than that of the latter, which shows that compared with the CBD+THC group, the CBD+CBG group can better improve vitality of the dopaminergic neuronal cells (see B and C in FIG. 2); furthermore, since CBG does not have psychoactivity and addiction, the side effect of the CBD+CBG group is greatly reduced.

Example 2: Influence of Compositions of Different Proportions of CBD+CBG on Cell-Induced Differentiation Example 1 revealed that the CBD+CBG combination had the optimal effect in promoting viability and secretion capacity of dopaminergic neurons; however, Example 1 only illustrated the effect of the CBD+CBG combination with a mass ratio of 1:1. Therefore, experiments on the compositions of different proportions of CBD+CBG were further designed to seek for the proportional combination that had the optimal effect in activating dopaminergic neurons.
(1) Experiment Process
1. Preparing Culture Mediums Basal medium 1, basal medium 2, induction medium 1 and induction medium 2 were prepared according to the formulae in Example 1, respectively; and then, the prepared mediums were sterilized via membrane filters for later use.
2. Culturing HDF38 Fibroblasts After the purchased HDF38 fibroblasts were resuscitated and cultured, they were subcultured in twelve 6 cm culture dishes including basal medium 1, wherein each culture dish included 80,000 HDF38 fibroblasts, which were cultured in a 5% $CO_2$ incubator at 37° C. After 3 days of culture, induced-differentiation of the cells were performed.
3. Inducing Differentiation of HDF38 Fibroblasts The above cells were divided into 12 groups to be subjected to induced differentiation. The experimental method was the same as relevant operations in Example 1. Designs of different proportions of CBD and CBG were shown in Table 2 below, in which CBD was added as 1 μg/10 ml medium.

During the process of induced differentiation, the cell changes were observed under a microscope (ZEISS AXIO observer) every day and recorded by photos.
4. Detecting the Relative Expression Level of DA-Related Factors.

Figure 3A:
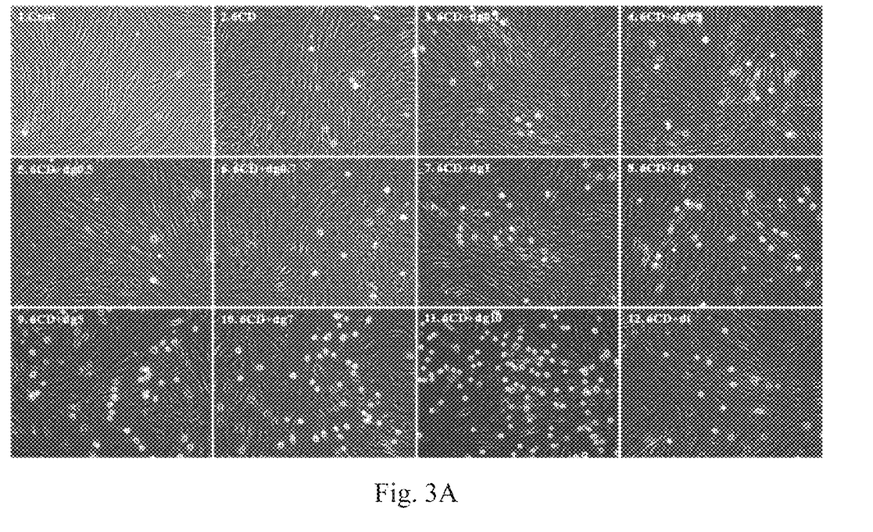
Figure 3B:
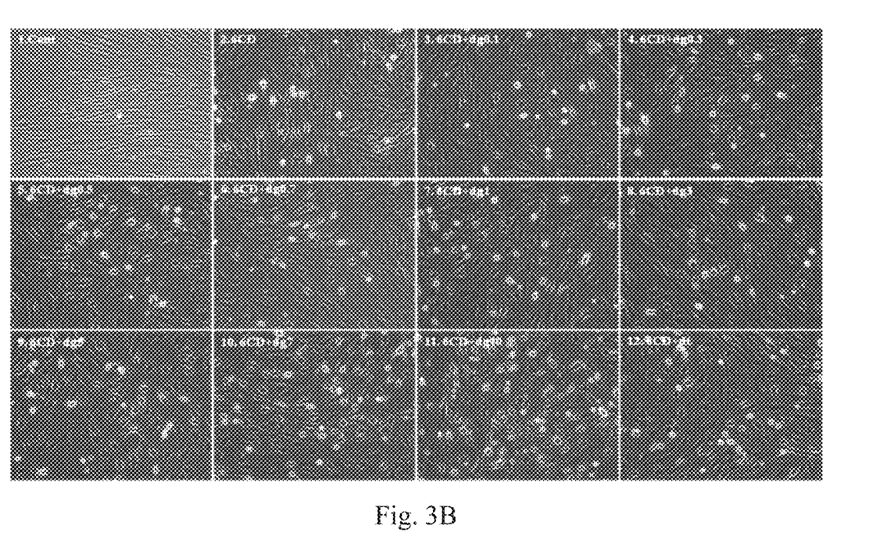
Figure 3C:
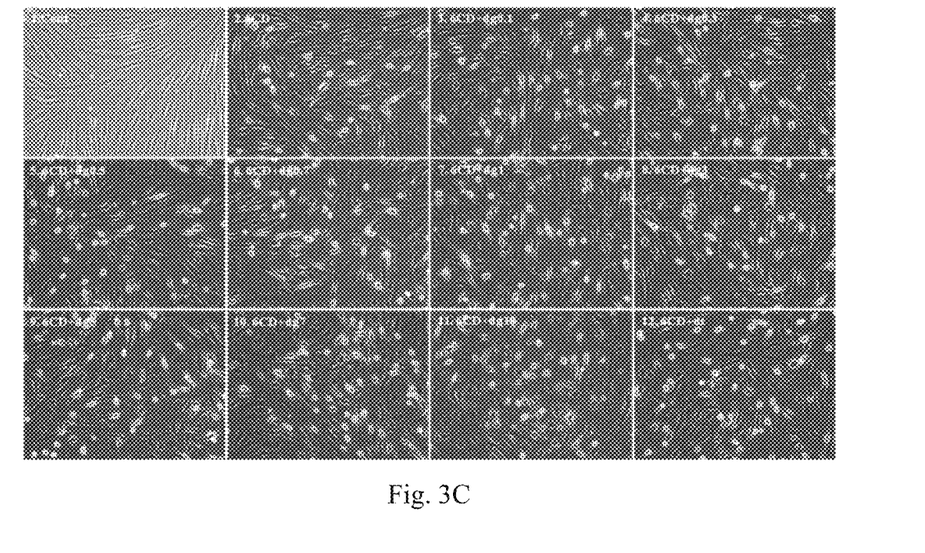

After 13 days of induced differentiation and culture, the cells were collected, and the Total RNA was extracted from the cells using TRIzol general reagent (Tiangen Biotech, Beijing, China), and the Total RNA was synthesized into complementary DNA (cDNA). The relative expression levels of DA-related factors Nurr1, TH-2 and Pitx3 in the cells were detected by quantitative real-time PCR with SYBR Green fluorescent dye.
(2) Experiment Results:

In FIG. 3, A~C show the cell morphology of each group on the $4^{th}$, $7^{th}$ and $13^{th}$ day of induced culture, respectively. The results show that on the $4^{th}$ day of induced culture, production of neurons could be observed in the cells of each culture group, and the number of neurons increased with the increase of CBG added in the medicine, indicating that a high concentration of CBG can increase the rate of inducing the fibroblasts to differentiate to neurons (FIG. 3A). However, after one week of induced culture, the cells of two groups (with a mass ratio of 1:7 and 1:10, respectively) with a high concentration of CBG died in different degrees, while the cells of other induced differentiation groups did not die, indicating that a high concentration of CBG would cause medicine toxicity and then lead to cell death. Therefore, under the CBD concentration in this experiment, a safe mass ratio of CBD to CBG in a cannabinoid composition is not higher than 1:5 (B and C in FIG. 3).

Figure 4A:
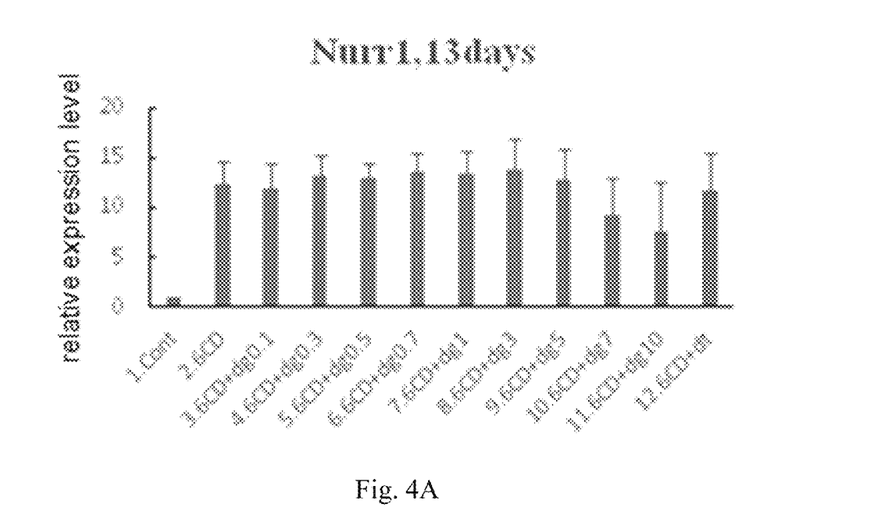
Figure 4B:
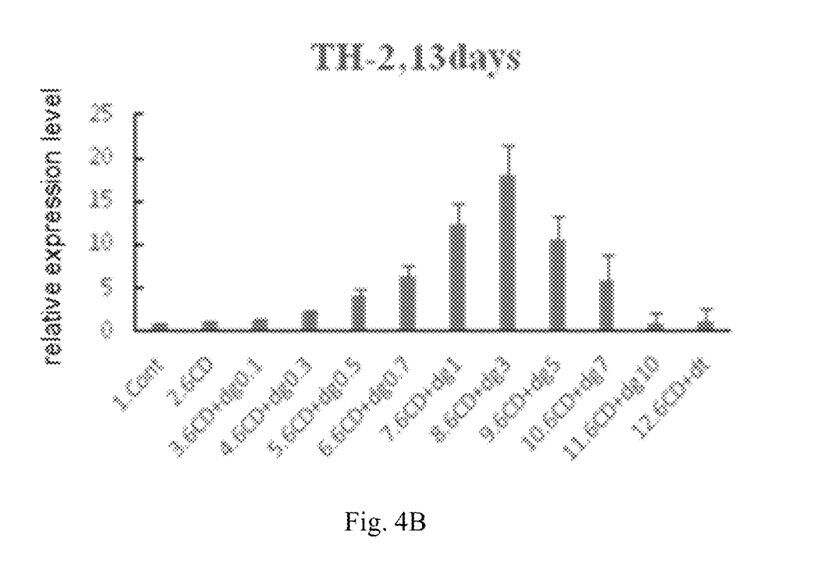
Figure 4C:
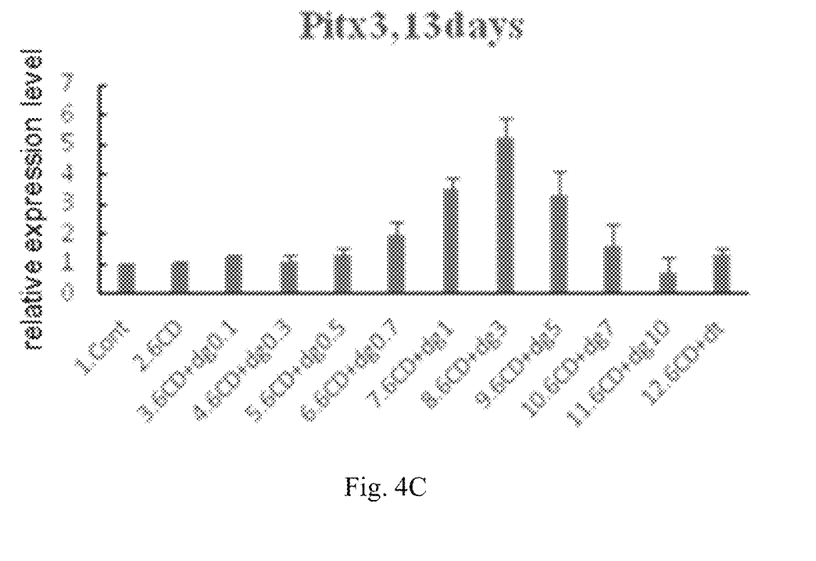

FIG. 4 is comparison chart of expression levels of DA-related factors in respective groups of cells. As shown in FIG. 4, when the mass ratios of CBD and CBG are 1:1, 1:3 and 1:5, respectively, the expression levels of TH-2 and Pitx3 are markedly higher than the control group and other

TABLE 2

Experimental Designs of Different Proportions of CBD + CBG Combinations

| No. Group # | Culture Medium | Medicines to-be-tested and their proportions (mass ratio) |
|---|---|---|
| 1 Non-differentiated group | Basal Medium 2 | N/A |
| 2 Differentiated control group | Induction mediums 1, 2 | N/A |
| 3 Differentiated + 1 CBD + 0.1 CBG Group | | CBD:CBG = 1:0.1 |
| 4 Differentiated + 1 CBD + 0.3 CBG Group | | CBD:CBG = 1:0.3 |
| 5 Differentiated + 1 CBD + 0.5 CBG Group | | CBD:CBG = 1:0.5 |
| 6 Differentiated + 1 CBD + 0.7 CBG Group | | CBD:CBG = 1:0.7 |
| 7 Differentiated + 1 CBD + CBG group | | CBD:CBG = 1:1 |
| 8 Differentiated + 1 CBD + 3 CBG Group | | CBD:CBG = 1:3 |
| 9 Differentiated + 1 CBD + 5 CBG Group | | CBD:CBG = 1:5 |
| 10 Differentiated + 1 CBD + 7 CBG Group | | CBD:CBG = 1:7 |
| 11 Differentiated + 1 CBD + 10 CBG Group | | CBD:CBG = 1:10 |
| 12 Differentiated + CBD + THC group | | CBD (1 μg/ 10 ml culture medium) and THC (0.2 μg/10 ml culture medium) | experimental groups, wherein the expression levels of TH-2 and Pitx3 are the highest when the ratio is 1:3.

Example 3: Influences of Different Proportions of CBD+CBD+CBN Compositions on Cell Differentiation Example 2 shows that when the mass ratio of CBD to CBG is 1:1 and 1:3, there achieves a better effect in activating the dopaminergic neurons. Therefore, based on the two ratios, experiments on different portions of CBD, CBG and CBN combinations were further designed to seek for the optimal combination and ratio in dopaminergic neuron activation.

(1) Experiment Process

1. Preparing Culture Mediums

Basal medium 1, basal medium 2, induction medium 1 and induction medium 2 were prepared according to the formulae in Example 1, respectively; the prepared mediums were sterilized via membrane filters for later use.

2. Culturing of HDF38 Fibroblasts

After the purchased HDF38 fibroblasts were resuscitated and cultured, they were subcultured in ten 6 cm culture dishes including basal medium 1, wherein each culture dish included 80,000 HDF38 fibroblasts, which were cultured in a 5% $CO_2$ incubator at 37° C. After 3 days of culture, induced-differentiation of the cells were performed.

3. Inducing Differentiation of HDF38 Fibroblasts

The above cells were divided into 10 groups to be subjected to induced differentiation. The experimental method was the same as relevant operations in Example 1. Designs of different proportions of CBD and CBG were shown in Table 3 below, in which CBD was added as 1 μg/10 ml medium.

els of DA-related factors Nurr1, TH-2 and Pitx3 in the cells were detected by quantitative real-time PCR with SYBR Green fluorescent dye.

(2) Experiment Results

Figure 5A:
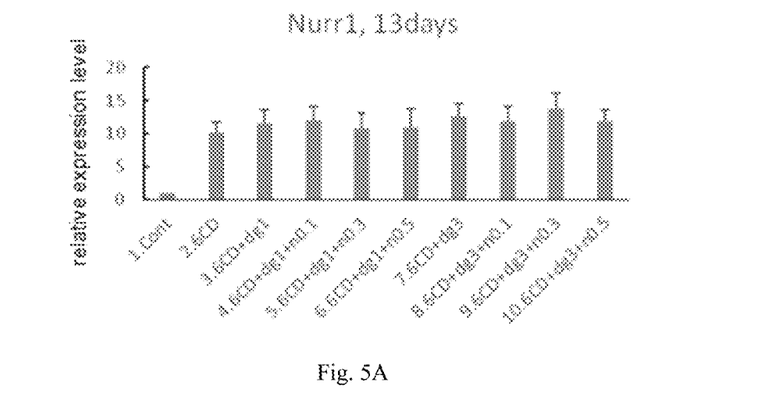
Figure 5B:
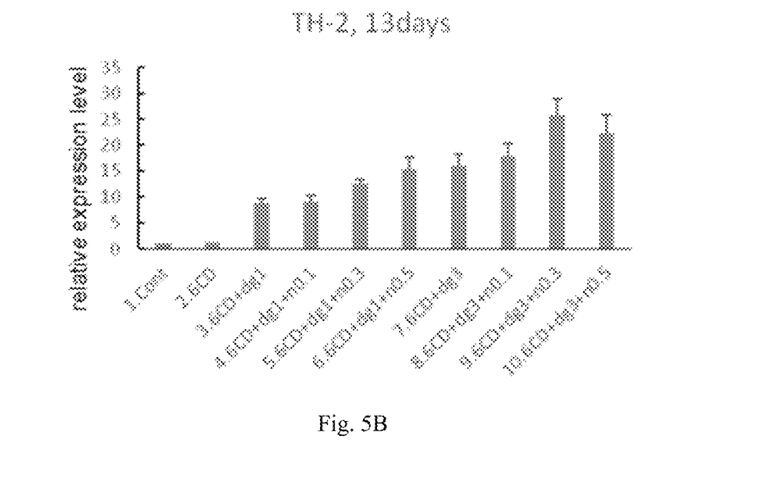
Figure 5C:
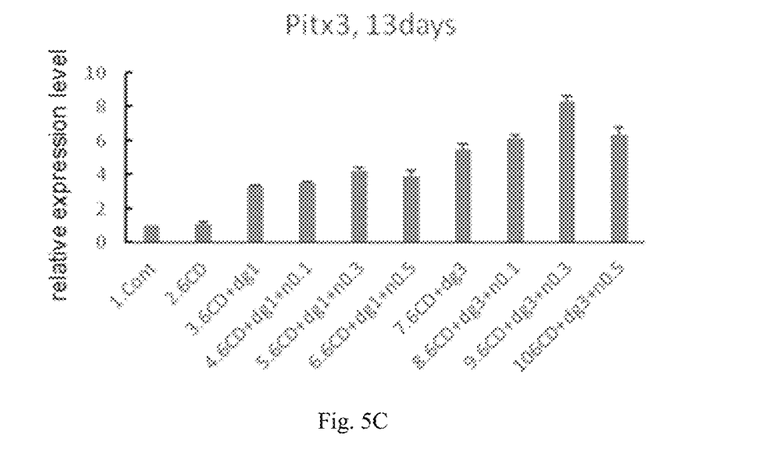

FIG. 5 is comparison chart of expression levels of the DA-related factors in respective groups of cells. The results show that adding CBN to CBD and CBG could further promote the vitality of the cannabinoid composition in activating dopaminergic neuronal cells. When the mass ratio of CBD to CBG in the CBD+CBG+CBN composition is 1:3, the expression levels of TH-2 and Pitx3 are higher than those under the mass ratio of CBD to CBG is 1:1, which proves the conclusion of Example 2 again. Furthermore, when CBD:CBG:CBN (mass ratio) is 1:3:0.3, the expression levels of TH-2 and Pitx3 were the highest, with the optimal vitality in activating the dopaminergic neuronal cells.

The 8 #Composition in Example 2 of the present disclosure was tested clinically and observed clinically. Specific results are shown below:

1. Clinical Data 14 patients were tested, wherein the youngest patient was 55 years old, and the eldest patient was 93 years old. Among the patients, there were 5 male patients and 9 female patients; the shortest pathogenesis was 1 year and the longest was about 15 years. 10 of the patients suffered PD and 4 suffered AD. Clinical examination: All cases were diagnosed according to relevant criteria of the state and industry associations.

2. Treatment Method

The medicine (sublingual drop, 2 ml per bottle, each bottle containing active ingredients of 10 mg CBD+30 mg CBG) prepared from No. 8 cannabinoid composition in Example 2 of the present disclosure was administered once

TABLE 3

Experimental Designs of Different Proportions of CBD + CBG + CBN Combination

| No. | Group # | Culture Medium | Medicines to be tested and their proportions (mass ratio) |
|---|---|---|---|
| 1 | Non-differentiated group | Basal Medium 2 | N/A |
| 2 | Differentiated control group | Induction mediums 1, 2 | N/A |
| 3 | Differentiated + 1 CBD + 1 CBG Group | | CBD:CBG = 1:1 |
| 4 | Differentiated + 1 CBD + 1 CBG + 0.1 CBN Group | | CBD:CBG:CBN = 1:1:0.1 |
| 5 | Differentiated + 1 CBD + 1 CBG + 0.3 CBN Group | | CBD:CBG:CBN = 1:1:0.3 |
| 6 | Differentiated + 1 CBD + 1 CBG + 0.5 CBN Group | | CBD:CBG:CBN = 1:1:0.5 |
| 7 | Differentiated + 1 CBD + 3 CBG Group | | CBD:CBG = 1:3 |
| 8 | Differentiated + 1 CBD + 3 CBG + 0.1 CBN Group | | CBD:CBG:CBN = 1:3:0.1 |
| 9 | Differentiated + 1 CBD + 3 CBG + 0.3 CBN Group | | CBD:CBG:CBN = 1:3:0.3 |
| 10 | Differentiated + 1 CBD + 3 CBG + 0.5 CBN Group | | CBD:CBG:CBN = 1:3:0.5 |

During the process of induced differentiation, the changes of cells were observed under a microscope (ZEISS AXIO observer) every day and recorded by photos.

4. Detecting the Relative Expression Levels of DA-Related Factors.

After 13 days of induced differentiation and culture, the cells were collected, and the Total RNA was extracted from the cells using TRIzol general reagent (Tiangen Biotech, Beijing, China), and the Total RNA was synthesized into complementary DNA (cDNA). The relative expression levor twice a day, once every 0.5-1 hour before going to bed, or once respectively at noon and before going to bed. The medicine was administered sublingually, i.e., applied under the tongue for about 60 seconds and then swallowed. Four weeks constitute one course of treatment, but dosage used during the course varies with conditions.

3. Criteria of Evaluating Therapeutic Effects

Improvement: the patient, bystander or medical examinations show that the symptoms of the patient have been alleviated, and/or his/her autonomous behaviors and consciousness have been enhanced.

Remarkable improvement: the patient, bystanders or medical examinations show that the symptoms of the patient are notably alleviated, and/or his/her autonomous behaviors and consciousness are notably enhanced (for example, the symptoms of Parkinson's disease are improved from stage 4 to stage 3).

Unnoticeable: The patient, bystander or medical examinations all deny that the symptoms have been alleviated or his/her autonomous behaviors and consciousness have been enhanced after taking the medicine.

5. Treatment Result

About 29% of patients (4 patients) got initial improvement in symptoms within the first week of taking the medicine, 64% of patients (9 patients) got improvement in symptoms within 2 weeks, and 79% of patients (11 patients) got notable improvement in symptoms within the first course of treatment. By far, about 14% of patients (2 patients) have no noticeable improvement effect, of which 1 patient administered it for 2 weeks and the other one administered it for 5 weeks. The improvement rate was about 86%.

No obvious side effects were found in all patients, and about 43% of patients (6 patients) reported partial drowsiness symptoms.

The cases listed in the present disclosure were all provided to preliminarily prove the effect of the present disclosure at the present stage, and the patients volunteered to take the medicine. Due to the characteristics of neurodegenerative diseases such as Parkinson's disease and Alzheimer's disease, the description of the medical history and its effect was based on the description from patients or their family, which might be subjective or not rigorous enough, but the cases and therapeutic effects are all real. As the case effects were not described by professionals in the medical field, the technical effects of various aspects of the cases do not represent authoritative medical diagnosis results.

Case 1

GAO: Male, 85 years old, a retired doctor from Rizhao, Shandong, was diagnosed with Parkinson's disease in 2017.

Medical history: started from 2012, slow movement, facial expressionless, and then the symptom became more and more serious. He found himself difficult in fine movement, and his limbs stiff and bent. He can only do small broken steps in walking. He also suffered from constipation, oily head and face, etc. In 2017, hospitalization examination: masked face, flustered gait, static tremor of hands, excessive muscle tension of limbs, muscle strength of limbs of grade 5. He was diagnosed with Parkinson's disease. After taking the medicine according to the doctor's advice for 4 years, the tremor has eased, but the facial expression was not improved, and gradually became serious, with serious drooling, slow and difficult in walking, unable to walk without crutches, and self-reported inability to walk.

Treatment: From July, 2021, take the medicine prepared by the No. 8 composition in Example 2 of the present disclosure, once a day before going to bed, one bottle at a time. He had taken the medicine continuously for 5 weeks.

Results: After taking the medicine for one week, the patient's dull eyes were improved, his facial expressions were richer. He can sometimes walk without crutches. The symptom of his limbs and fine movements were obviously improved, and he recovered his self-care ability of cutting nails and peeling pills after about two years' interruption. The patient is drowsy after taking the medicine. Drink tea to relieve drowsiness.

Case 2

XU: Female, 83 years old, from Zhengzhou, Henan Province, was diagnosed with Parkinson's disease in 2019.

Medical history: Since 2014, the patient's movement has gradually slowed down, her limbs have become stiff, her sleep time has decreased, and she experienced sleep disorders and other phenomena. Since 2018, her situation had worsened obviously, and she was difficult to walk, enunciate and pronounce words, and the tongue was not easy to control. In 2019, she was diagnosed with Parkinson's disease.

Treatment: From July, 2021, take the medicine prepared by the No. 8 composition in Example 2 of the present disclosure, once a day before going to bed, one bottle at a time. She had taken the medicine continuously for 3 weeks.

Results: The patient's self-control ability began to improve in the second week after taking the medicine. The symptoms of uncontrolled drooling and tongue have obviously improved, and the time of self-standing walking has obviously increased. The single self-walking time has increased from less than 10 minutes to more than 20 minutes. Her sleep time is obviously increased and emotion is stable.

Case 3

JI: Female, 93 years old, from Heilongjiang, was diagnosed with Parkinson's disease in early 2021.

Medical history: Since 2015, limb rigidity and involuntary tremor appeared. In 2020, the illness was obviously aggravated. She was unable to walk independently, lying in bed for a long time, often cramped in the limbs, basically unable to complete fine movements such as eating and taking medicine, emotionally instable, and irritable. In early 2021, she was diagnosed with Parkinson's disease.

Treatment: From May 2021, take the medicine prepared by the No. 8 composition in Example 2 of the present disclosure, once a day before going to bed, one bottle at a time. She had taken the medicine continuously for 11 weeks.

Results: In the second week after taking the medicine, the rigidity of limbs was obviously relieved, the frequency and amplitude of involuntary tremor were reduced, and the spasm of limbs was reduced. After 11 weeks of administration, the patient could autonomously stand on the wall for nearly 5 minutes. Articulate clearly, pronounce correctly, and talking to people tend to be normal. Sleep time increased and emotion was stable.

Case 4

DAI: Female, 81 years old, Malaysian, diagnosed with Alzheimer's disease in 2017.

Medical history: Since 2014, the patient has experienced severe memory deterioration, unable to open the door with a key, likes to hide things and is suspicious. Since 2017, the illness has obviously worsened, with cognitive impairment. She can't recognize her relatives and friends, and cannot recall what she just did. She was treated with non-medicine treatments such as diet treatment and lifestyle treatment, supplemented by Donepezil(Aricept). After a year without obvious improvement, herbal medicine and dietotherapy were adopted instead, but the effect was still unsatisfactory.

Treatment: From May 2021, take the medicine prepared by the No. 8 composition in Example 2 of the present disclosure, once a day before going to bed, one bottle at a time. She had taken the medicine continuously for 11 weeks.

Results: After taking it for one week, the patient's short-term memory began to improve, and she could chat with the nurse normally. After about 3-4 weeks of use, her memory began to recover, and she can recognize her family and friends. The medicine had been administered for 11 weeks now, and the recovery was good, and her memory of one year ago can be recalled. No adverse reaction was reported.

Case 5

SHEN: female, 68 years old, from Guangdong, was diagnosed with Alzheimer's disease in early 2021.

Medical history: The patient was admitted to hospital in early 2021 because of "memory loss for more than 3 years, the symptom was aggravated for one and a half years". No obvious abnormalities were found in routine urine and blood examination, the seven-tumor-marker examination and quadruple myocardial injury. Craniocerebral CT: Multiple lacunar infarction in bilateral basal ganglia and corona radiata; White matter degeneration; Brain atrophy. Magnetic MRI of brain: lacunar infarction, white matter degeneration, brain atrophy. There was no obvious abnormality in other inspections. After being diagnosed with Alzheimer's disease, the patient used medication such as Rivastigmine capsule and Memantine for about 4 months, without obvious improvement.

Treatment: From May 2021, take the medicine prepared by the No. 8 composition in Example 2 of the present disclosure, once a day before going to bed, one bottle at a time.

Results: In the $3^{rd}$ week after taking the medicine, the patients' instantaneous memory was obviously enhanced, and she could recall the events in the past 3 days and the main events in the past 1 week. After taking it for 11 weeks, her memory was obviously improved, and the obstacles of daily conversation and memory were obviously reduced. She began to sleep during the day, with mild drowsiness.

Case 6

WANG: Male, 87 years old, Malaysian, diagnosed with Alzheimer's disease in 2013.

Medical history: Since 2007, the patient has experienced memory loss and other phenomena. In 2013, the patient was diagnosed with Alzheimer's disease and started treatment. In the first two years of treatment, cognitive decline such as memory decline was alleviated, but the effect quickly subsided and the condition continued to deteriorate. For about ten years, treatment has played a certain role in delaying the deterioration of patients' symptoms, but it has never improved the patients' conditions.

When the patient was first met, he didn't respond to our greetings, and he couldn't understand most language semantics, such as "put it under the tongue and hold it" and other medication instructions. Usually, when he was in bed or in a wheelchair, he could stand, but he had poor self-action ability and basically no self-care ability. Poor identification ability, unable to recognize his loved ones.

Treatment: From June 2021, take the medicine prepared by the No. 8 composition in Example 2 of the present disclosure, once a day before going to bed, one bottle at a time.

Results: After taking it for one week, the patient became sober and understood the language such as medication instructions. After taking it for 9 weeks, the recovery is good. He could chat freely with his neighbors downstairs and introduce his clothes and shopping. He began to remember his grandson's mobile phone number, and most of common communications has become normal.

To sum up, the present disclosure applies the experimental method of inducing differentiation of fibroblasts to dopaminergic neurons in order to detect the influences of CBD, CBG, THC and various combinations thereof on the induced differentiation of fibroblasts to dopaminergic neurons, finding that a CBD+CBG composition is optimal to promote induced differentiation to dopaminergic neurons, can significantly improve the viability and dopamine-secreting capability of dopaminergic neurons, and thus can be applied to medicines for treating neurodegenerative diseases, such as Parkinson's disease; further, because it is free of the addictive substance THC, side effects are significantly reduced. Further experiments on different proportions of CBD+CBG combination were designed, finding that when the mass ratio of CBD and CBG was 1:1~1:5, the cannabinoid composition could significantly improve the vitality of dopaminergic neuronal cells, and when the ratio was 1:3, the effect was the best. Experiments on different portions of CBD+CBG+CBN combination were further designed, finding that adding CBN could further improve the effect of the cannabinoid composition in activating the vitality of the dopaminergic neuronal cells. When CBD:CBG:CBN (mass ratio) is 1:3:0.3, the effect of activating the vitality of the dopaminergic neuronal cells is the optimal.

Although the contents of the present disclosure have been described in detail through the foregoing preferred embodiments, it should be understood that the depictions above shall not be regarded as limitations to the present disclosure. After those skilled in the art having read the contents above, many modifications and substitutions to the present disclosure are all obvious. Therefore, the protection scope of the present disclosure should be limited by the appended claims.

We claim:

1. A cannabinoid composition, comprising: cannabidiol and cannabigerol, wherein a mass ratio of the cannabidiol to the cannabigerol is between 1:1 and 1:10 and is not 1:1.

2. The cannabinoid composition according to claim 1, wherein the mass ratio of the cannabidiol to the cannabigerol ranges is between 1:1 to 1:3, or from 1:3 to 1:5, or from 1:5 to 1:7.

3. The cannabinoid composition according to claim 1, wherein the mass ratio of the cannabidiol to the cannabigerol is 1:3.

4. The cannabinoid composition according to claim 1, wherein the cannabinoid composition further comprises cannabinol.

5. The cannabinoid composition according to claim 4, wherein the mass ratio of the cannabidiol to the cannabinol ranges from 1:0.05 to 1:1.

6. The cannabinoid composition according to claim 4, wherein the mass ratio of the cannabidiol to the cannabinol ranges from 1:0.1 to 1:0.5.

7. The cannabinoid composition according to claim 4, wherein a mass ratio between the cannabidiol, the cannabigerol, and cannabinol is 1:3:0.3.

8. A method comprising administering the cannabinoid composition according to claim 1 to a subject for treating a neurodegenerative disease in the subject.

9. The method according to claim 8, wherein the neurodegenerative disease is Parkinson's disease, Alzheimer's disease or dementia with Lewy bodies.

10. The method according to claim 8, wherein the cannabinoid composition is administered so as to promote development and maturity of dopaminergic neuronal cells, prevent shedding of the dopaminergic neuronal cells, and/or enhance viability of the dopaminergic neuronal cells.

11. The method according to claim 8, wherein the cannabinoid composition is administered so as to enhance dopamine-secreting capability of dopaminergic neuronal cells.

12. A pharmaceutical composition for treating neurodegenerative diseases, wherein the pharmaceutical composition comprising: the cannabinoid composition according to claim 1 and a pharmaceutically acceptable carrier.

13. The pharmaceutical composition according to claim 12, wherein a dosage form of the pharmaceutical composition is chosen from the group consisting of an oil agent, granule, tablet, pulvis, capsule, pill, powder, oral liquid, gel, spray, and aerosol.

14. A pharmaceutical kit for treating neurodegenerative diseases, the pharmaceutical kit comprising: the cannabinoid composition according to claim 1.

* * * * *